United States Patent [19]

Miller

[11] Patent Number: 5,266,474
[45] Date of Patent: Nov. 30, 1993

[54] BALANCED INDUCIBLE TRANSCRIPTION SYSTEM

[75] Inventor: Harvey I. Miller, Pleasant Hill, Calif.

[73] Assignee: Genentech, Inc., South San Francisco, Calif.

[21] Appl. No.: 719,056

[22] Filed: Jun. 21, 1991

Related U.S. Application Data

[60] Continuation of Ser. No. 568,252, Aug. 15, 1990, abandoned, which is a division of Ser. No. 65,794, Jun. 24, 1987, abandoned.

[51] Int. Cl.$^5$ .................. C12N 15/00; C12N 9/64; C12N 1/21
[52] U.S. Cl. ..................... 435/226; 435/252.33; 435/172.3
[58] Field of Search ............. 435/172.3, 212, 226, 435/252.3; 536/27, 27.3

[56] References Cited

U.S. PATENT DOCUMENTS

| | | | |
|---|---|---|---|
| 4,338,397 | 7/1982 | Gilbert et al. | 435/69.1 |
| 4,643,969 | 2/1987 | Inouye et al. | 435/69.1 |
| 4,680,262 | 7/1987 | Bochner et al. | 435/69.1 |
| 4,766,075 | 8/1988 | Goeddel et al. | 435/240.2 |

FOREIGN PATENT DOCUMENTS

| | | |
|---|---|---|
| 877012 | 9/1989 | Australia . |
| 0077569 | 4/1983 | European Pat. Off. . |
| 0093619 | 9/1983 | European Pat. Off. . |
| 123544 | 10/1984 | European Pat. Off. . |
| 0136907 | 4/1985 | European Pat. Off. . |
| 0159779 | 10/1985 | European Pat. Off. . |
| 0178863 | 4/1986 | European Pat. Off. . |
| 0207459 | 6/1986 | European Pat. Off. . |
| 0225286 | 6/1987 | European Pat. Off. . |
| 0335567 | 3/1989 | European Pat. Off. . |
| 0236209 | 9/1998 | European Pat. Off. . |
| 8706611 | 11/1987 | PCT Int'l Appl. . |

OTHER PUBLICATIONS

Herrin et al., Gene vol. 32 pp. 349-356.
Buell et al., in Maximizing Gene Expression, ed. by Reznikoff et al., Butterworth Publ., Stoneham, Mass. 1986, pp. 345-363.
Lewis, in Genes, John Wiley and Sons, New York, 1985, pp. 683 and 687.
Belin et al., *Eur. J. Biochem.* 148:225-232 (1985).
Ben-Bassat, A. et al., *J. Bacteriology* 169:751-757 (Feb. 1987).
Fuerst et al., *P.N.A.S. USA* 83:8122-8126 (1986).
Goeddel, D. et al., *Nature* 281:544-548 (1979).
Harris, T. et al., *Mol. Biol. Med.* 3:279-292 (1986).
Kagatani, H. et al., *FEBS Letter* 189:145-149 (1985).
Lemmont et al., *DNA* 4(5):419-428 (1985).
Leytus et al., *P.N.A.S. USA* 78(3):1485-1489 (1981).
Little et al., *Biochem.* 23(25):6191-6195 (1984).
Moss et al., *Chem. Abs.* 107:Abs.#128482d (1987).
Opdenakker et al., *Eur. J. Biochem.* 131:481-487 (1983).
Opdenakker et al., *Proc. Soc. Exp. Biol. & Med.* 182:248-257 (1986).
Pennica, D. et al., *Nature* 301:214-221 (1983).
*Promega Biotech*, Riboprobe Product Brochure (May 1, 1986).
Rijken et al., *thromb. & Haemost.* 54(4):788-791 (1985).
Sherman, F. et al., *BioEssays* 3(1):27-31 (1985).
*Stratagene T7 Polymerase Product Brochure* (Undated).
Studier et al., *J. Mol. Biol.* 189:113-130 (1986).
Tabor et al., *Chem. Abs.* 102:Abs.#144115p (1985).
Tabor et al., *Proc. Natl. Acad. Sci. USA* 82:1074-1078 (1985).

Primary Examiner—Richard A. Schwartz
Assistant Examiner—Nancy T. Vogel
Attorney, Agent, or Firm—Ginger R. Dreger

[57] ABSTRACT

A balanced constitutive inducible transcriptional control system is provided to facilitate the expression of polypeptides incompatible with recombinant host cells. Use of this system has, for the first time, made it possible to produce mature, unglycosylated human tissue plasminogen activator in prokaryotes which is water soluble and fully enzymatically active. In accordance with this invention, t-PA is produced by recombinant bacterial host cell culture in commercially significant amounts without in vitro renaturation and processing.

2 Claims, 2 Drawing Sheets

BALANCED INDUCIBLE TRANSCRIPTION SYSTEM

This is a continuation of application Ser. No. 07/568,252 filed on 15 Aug. 1990, now abandoned, which is a divisional application of application Ser. No. 07/065,794 filed on 24 Jun. 1987, now abandoned.

BACKGROUND

This invention relates to the synthesis of heterologous polypeptides in recombinant host cells. In particular, this relates to the secretion of mature human plasminogen activator proteases from bacterial transformants.

Inducible promoters are well known. Such promoters are characterized by the ability to increase the rate of transcription of genes under their control upon a change in the environment of the cell, typically the concentration of inorganic ions or nutrients, or a change in a physical condition such as the temperature of cultivation. Such promoters include the E. coli trp, E. coli lac and yeast acid phosphate, respectively, or the promoter controlled by the temperature sensitive lambda phage repressor (Harris, et al., infra). Inducible promoters have been employed to control the transcription of heterologous genes in recombinant cell culture. In this context, they serve to restrain transcription, and hence translation, of heterologous proteins that are known to be toxic to host cell or which are degraded proteolytically by the host cell. Induction from the promoter at a suitable phase in the recombinant culture therefore minimizes the contact of the host cell with the heterologous polypeptide, and vice versa.

Currently available inducible promoters all exhibit various constitutive levels of transcription, even when conditions are optimized for repression or deactivation of the promoter. For most recombinant systems this is not disadvantageous at the constitutive levels encountered because polypeptide losses to degradation are tolerable, toxicity is insufficient to seriously affect yields of heterologous polypeptide and/or polypeptide shunted into refractile bodies or other processing sinks is readily reactivated or reprocessed.

In an attempt to provide more control over induction of transcription of heterologous genes the T7 RNA polymerase system has been adapted to the synthesis of certain heterologous polypeptides in recombinant host cells.

This system, which has heretofore been extensively described per se. consists of an RNA polymerase that recognizes unique promoters present only in T7 DNA. None of these promoters are known to be transcribed by wild-type E. coli or mammalian RNA polymerases. This transcriptional system containing T7 RNA polymerase and the companion promoters is therefore highly selective, and the selectivity is enhanced by placing the T7 RNA polymerase gene under the control of the lac UV5 inducible promoter recognized by the host cell RNA polymerase (Studier et al., "J. Mol. Biol." 189:113-130 [1986]; Tabor et al., "Proc. Natl. Acad. Sci. USA" 82:1074-1078 [1985]). Tabor et al., (op. cit.), finding that expression of T7 RNA polymerase was excessive in their system, inserted a transcriptional terminator 5' to the polymerase gene in order to suppress its constitutive expression. This also reduced the inductive capability of the system. A mammalian cell expression system for recombinant cytoplasmic proteins using the T7 RNA polymerase has been described by Fuerst et al., "Proc. Natl. Acad. Sci. USA" 83:8122-8126 (1986). This system as presently constituted, notwithstanding its promise for improving the control of transcription from genes under its aegis, has not proven useful for controlling the expression of certain polypeptides, nor have conventional inducible promoters. In each instance, the constitutive level of transcription from these conventional systems has proven to be incompatible with the host cell and stability of the gene encoding the heterologous protein. The reasons for this incompatibility have been poorly understood. Typically, the art has simply observed that secretion of the desired protein was poor or nonexistent without delving into the mechanisms responsible.

Many heterologous polypeptides have been secreted from microbial hosts. Typically, a chimeric gene is constructed in which a signal sequence is ligated 5' to the codon for the mature amino terminus of the desired polypeptide. This gene is used to transform microbial host, the host cultured, and the secreted mature polypeptide recovered from the host cell periplasm or, occasionally, the culture medium. Representative general methods for the secretion of heterologous polypeptides from bacteria and yeast are described in Gilbert et al., U.S. Pat. No. 4,338,397 and EP 127,304 or EP 88,632, respectively. It is known to use signal sequences obtained from the host cell ("host-homologous signals"), or signals that are heterologous to the host cell (including the use of variant signals or signals which are native to the heterologous polypeptide). More recently, signals have been directly linked to the mature N-terminus of the heterologous polypeptide, although it also is conventional to link the heterologous polypeptide, together with a portion of its own signal, to the N-terminus of a host-homologous signal. In the alternative, heterologous polypeptide has been linked to the C-terminus of a host-homologous signal containing a portion of the homologous protein normally secreted under the control of the homologous signal.

Previous attempts to provide a microbial host-vector system for the secretion of human plasminogen activator have been unsuccessful, notwithstanding that commercial quantities of tissue type human plasminogen activator (t-PA) are readily secreted from transformants of mammalian cell lines. Bacteria, which do not glycosylate proteins, were first used as hosts for the recombinant synthesis of t-PA. See EP 93,619 and Harris et al. ("Mol. Biol. Med." 3:279-292 [1986]). Harris et al. describe the expression in E. coli of t-PA from a gene encoding N-methionyl t-PA. High levels of recombinant met t-PA did in fact accumulate in the Harris et al. E. coli hosts as insoluble refractile bodies, but little in the way of active enzyme could be recovered, despite extensive efforts to reactivate the enzyme by in vitro processing of the refractile bodies. These authors suggested that expression systems using vectors designed for secretion of proteins in E. coli or yeast may be more successful for making active enzyme under conditions where inclusion bodies are not formed. To date, this prophecy has proven equivocal in the case of yeast and false in the case of bacteria.

Lemontt et al. ("DNA" 4(6):419 [1985]) transformed yeast with t-PA preproteins bearing either the native human t-PA signal or the yeast acid phosphatase signal. Like the E. coli transformants of Harris et al., yeast were found to shunt most of the expressed protein into an insoluble, enzymatically-inactive reservoir (according to Lemontt et al. this occurred as a result of an associative interaction of the t-PA with cell membranes) without the secretion of soluble t-PA into the culture medium. Lemontt et al. did not describe whether the N-termini of the t-PA prepro constructions were properly processed, nor whether the minor proportion of soluble t-PA that was obtained was originally lodged in the periplasm or the cytoplasm.

EP 123,544 reported the secretion of human t-PA by the use of the alpha factor signal. The t-PA was divided equally between the cells (20 μg/l) and the cultured medium (20 μg/l).

On the other hand, EP 177,343 observes that little or no human t-PA activity could be obtained from *E. coli* transformants in which DNA encoding the alkaline phosphatase signal was fused to DNA encoding mature t-PA under the transcriptional control of the alkaline phosphatase promoter.

The mechanism responsible for the apparent inability of bacteria to express and secrete human plasminogen activators in commercially significant quantities remain inapparent, although an apparent requirement for glycosylation of the human enzymes has been implicated. Belin et al. ("Eur. J. Biochem." 148:225-232 [1985]) reported the secretion of enzymatically active murine urokinase from *E. coli* host cells which apparently were transformed with murine preprourokinase, but native murine urokinase is not normally glycosylated. On the other hand, Opdenakker et al. ("Proc. Soc. Exp. Biol. Med." 182:248-257 [1986]) reported significant reductions in the enzymatic activity of secreted t-PA when oocyte transformants were incubated with tunicamycin in order to inhibit glycosylation, the residual enzymatic activity in the tunicamycin-treated oocyte preparations being attributable to partially glycosylated t-PA. Other studies reported in the same work demonstrated reductions in t-PA activity by 15 to 85% when glycosylated t-PA was digested with glycolytic enzymes. Consistent with these findings was an earlier report by Opdenakker et al. ("Eur. J. Biochem." 131:481-487 [1983]) that reticulocyte translation products of the t-PA gene were devoid of enzymatic activity, a phenomenon described by these authors as possibly the result of the inability of reticulocyte preparations to perform post-translational functions (processing and glycosylation). On the other hand, a report by Kagitani et al. ("FEBS" 189(1):145 [1985]) observes enzymatic activity in homogenates of *E. coli* transformants with DNA encoding des (1-44) "finger-domain" deleted variant t-PA.

If, as suggested by the art, secretion of enzymatically active plasminogen activators that normally are glycosylated will only occur when preplasminogen activators are processed by eukaryotic secretory mechanisms, then it should not be possible to recover commercially significant amounts of secreted enzymatically active plasminogen activators from prokaryotic cell structure.

Accordingly, it is an objective herein to identify problems responsible for the failure of certain host vector systems to produce desired polypeptides, in particular to stably secrete mature polypeptides from certain preproteins. Realization of this objective will lead to host-vector systems which will successfully and routinely secrete mature heterologous polypeptides.

An additional objective is to devise a method for the secretion of fully functional human plasminogen activators from prokaryotic cell culture.

It is further objective to provide a method for the secretion of human tissue plasminogen activator (ht-PA) from bacterial cell culture in commercially significant quantities.

In the method of this invention inducible transcriptional control system is used to express a desired host cell-incompatible heterologous polypeptide in recombinant host cell culture wherein the degree of constitutive expression of the polypeptide is balanced against cell incompatibility.

These and other objects of the invention will be apparent from the specification as a whole.

SUMMARY

The objects of this invention have been accomplished by a method comprising preparing DNA encoding a polypeptide which is heterologous to a host cell, placing the DNA into an expression vector under the transcriptional control of a balanced constitutive inducible transcriptional control system, transforming a host cell culture with the expression vector, culturing the cell culture to a predetermined cell density, inducing transcription from the DNA encoding said polypeptide, and recovering the polypeptide from the cell culture. The balanced system is obtained by placing the DNA under the transcriptional control of a first inducible promoter system having a first rate constitutive expression, determining the level of expression of the DNA, and thereafter (a) modifying the rate of constitutive expression of the first promoter system or (b) substituting a second inducible promoter system for the first inducible promoter system, the second promoter system having a rate of constitutive expression which is different from the first promoter system. Typically, if the constitutive level of expression under the control of the first promoter system is excessive one will observe little or no expression of the desired polypeptide, this generally developing over 10-30 generations of host cell replication. In this case the constitutive expression level is reduced by an appropriate manipulation of the first promoter system, e.g. increasing the level of repressor protein in the cell, or by replacing the first promoter system with another having a lower rate of constitutive expression. The promoter is referred to as a "system" in order to include regulatory genes, e.g. those encoding repressors, activators, or dedicated RNA polymerases, that influence transcription from the promoter per se. any one or more of which are manipulated in accordance with this invention.

The terms "balanced constitutive inducible system", "balanced constitutive inducible transcriptional control system", "balanced constitutive inducible promoter system" and "balanced constitutive transcriptional control system" as used throughout the specification refer to a transcriptional control system used to express a desired host cell-incompatible heterologous polypeptide in a recombinant host cell culture, comprising an uninduced inducible promoter, wherein the degree of constitutive expression of the polypeptide is balanced against cell incompatibility.

A balanced constitutive inducible system for the transcriptional control of ht-PA in recombinant prokaryotic host cells is provided by 1) modifying DNA 5' to the DNA encoding the T7 RNA polymerase so as to delete a region previously conferring low level constitutive transcriptional activity on the T7 RNA polymerase gene, 2) integrating the gene encoding T7 RNA polymerase, free of other T7 phage promoters, into the genome of the host cell and 3) inverting the T7 promoter in the expression vector so that it does not control the transcription of pBR322 beta-lactamase, thereby suppressing excessive penicillinase expression.

The inventor has observed that the failure to stably express heterologous proteins, particularly pre ht-PA in recombinant host culture frequently is attributable to the use of conventional promoters now found to be inappropriate for use with such proteins. The inventor has determined that transformants are stably maintained when the expression of heterologous preprotein is adjusted to a level compatible with host cell homeostasis, thus making it possible to obtain elevated levels of expression upon induction of transcription and translation at a predetermined point in the cultural growth cycle. Otherwise, it has been the inventor's experience that recombinant cells which are sensitive to heterologous protein toxicity (or that of its mRNA) experience selection pressure against the offending gene over 10–30 generations, resulting for example in retarded cell growth rates, the loss of the gene encoding the protein or, more often, selection for mutants in the protein or its operon that permanently abrogates proteins synthesis or results in synthesis of a mutant protein which may be of no commercial utility. Specifically, the improved T7 RNA polymerase balanced constitutive transcriptional control system provided herein now facilitates the stable cloning and expression of ht-PA and other polypeptides requiring similar constitutive expression levels.

The practice of this invention also facilitates the further development of high-yield secretion systems because cellular toxicity and plasmid instability are no longer factors impeding the study of other influences on the success of heterologous protein secretion, e.g., signal choice. For example, if a preprotein remains poorly processed by host cells when transcribed under the control of a balanced constitutive transcriptional control system then one skilled in the art will be taught to select one or more alternative secretion signals in order to determine which is best processed by the host cell in question. Paradoxically, the secretion of useful quantities of heterologous proteins may in some cases be facilitated by selecting a transcriptional control system that does not transcribe the desired gene at the maximally elevated levels favored by those skilled in the art, who have tended to search for and use the most powerful promoters available, but rather in selecting a control system that is balanced constitutively. Desired yields are obtained by providing inducibility in the system.

For the first time, water soluble, biologically active, unglycosylated mature t-PA has been obtained from prokaryotes by the use of a balanced constitutive inducible transcription control system. Surprisingly, the t-PA secreted from bacteria is present in commercially significant quantities (yields exceeding about 1 mg/l or 10 ng/$OD_{550}$ unit of culture) and exhibits high specific activity (comparable to that of t-PA from CHO cell transformants). This t-PA is secreted as a water soluble molecule, binds lysine and is fibrin activated, notwithstanding that the bacterial product is unglycosylated and in any case was produced by a method relying solely on microbial processing systems.

It appears that transcription from pret-PA genes in prokaryotic hosts must be very tightly regulated during the growth phase of pret-PA transformants, more so than has been possible by the use of conventional constitutive or inducible systems such as the heat sensitive λ repressor controlled promoter (Harris et al. op cit) or the alkaline phosphatase promoter and signal (EP 177,343), both of which failed to generate stable host/vector systems that would secrete useful quantities of t-PA. While cytoplasmic t-PA apparently is not toxic, t-PA destined for secretion is toxic to prokaryotes. In the preferred embodiment, stable t-PA secretion is accomplished by placing the t-PA gene under the transcriptional control of the T7 promoter and repressing transcription from the t-PA gene by the use of a host cell containing a novel T7 RNA polymerase DNA integrant which is itself under the transcriptional control of a tightly regulated inducible promoter. When the culture has reached the desired density then, optionally, transcription is induced from the T7 polymerase gene, and then ultimately from the t-PA gene. t-PA is rapidly synthesized and secreted from these transformants at high specific activity and yield.

In summary, therefore, the invention herein lies in providing a balanced constitutive inducible transcriptional control system and, in a preferred embodiment, finding that it is useful to employ such a system to control the expression of a heterologous preprotein such as t-PA. This provides for the first time a method for secreting mature, biologically active, unglycosylated t-PA from bacterial cell culture in commercially useful quantities at high specific activity.

DETAILED DESCRIPTION

Figure 1:
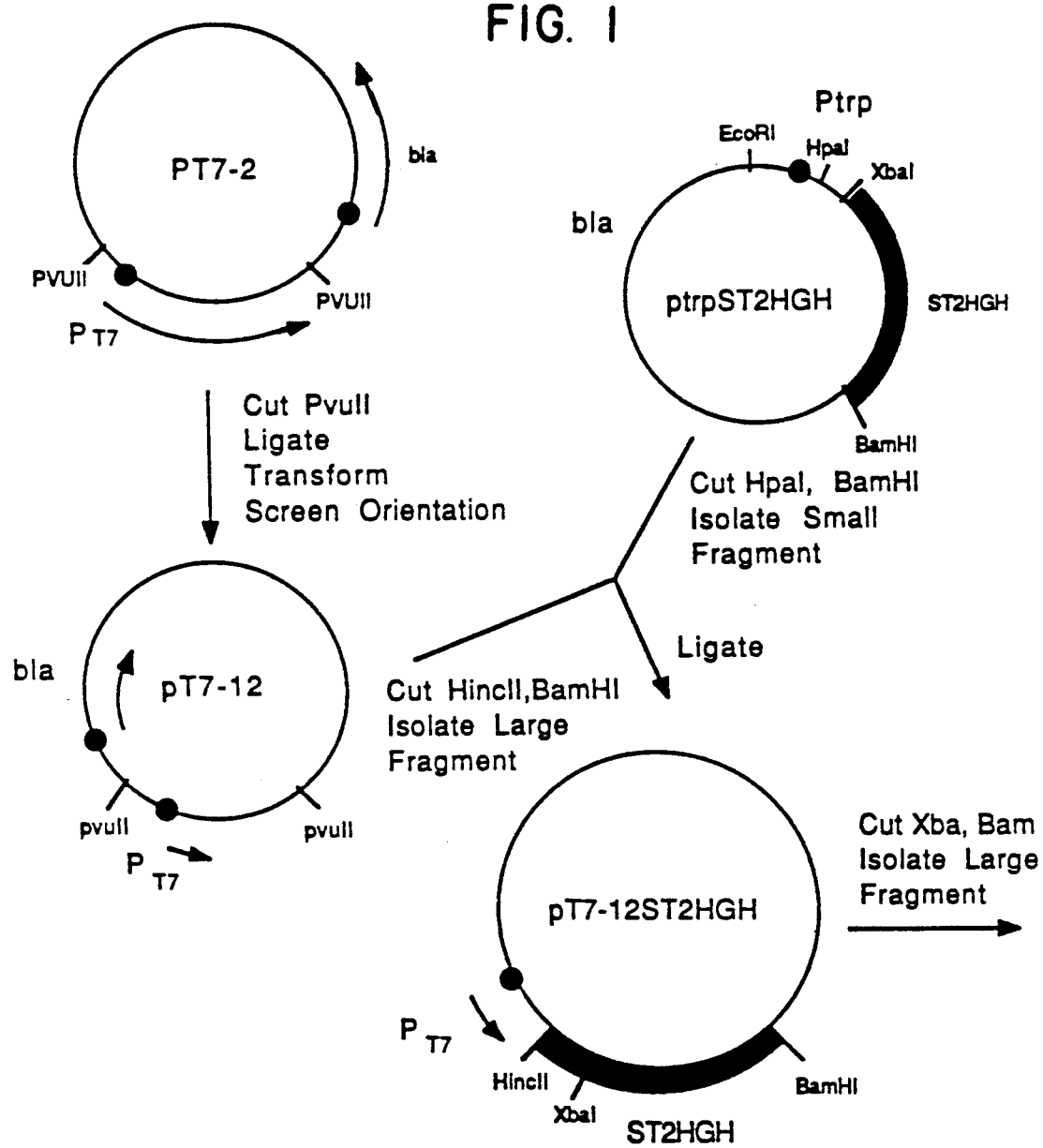
FIG. 1. depicts the construction of pT7-12, a plasmid providing the phi 10 promoter recognized by T7 polymerase ($P_{T7}$), and the construction of pT7-12ST2HGH, an intermediate plasmid which supplies the STII signal and phi 10.
Figure 2:
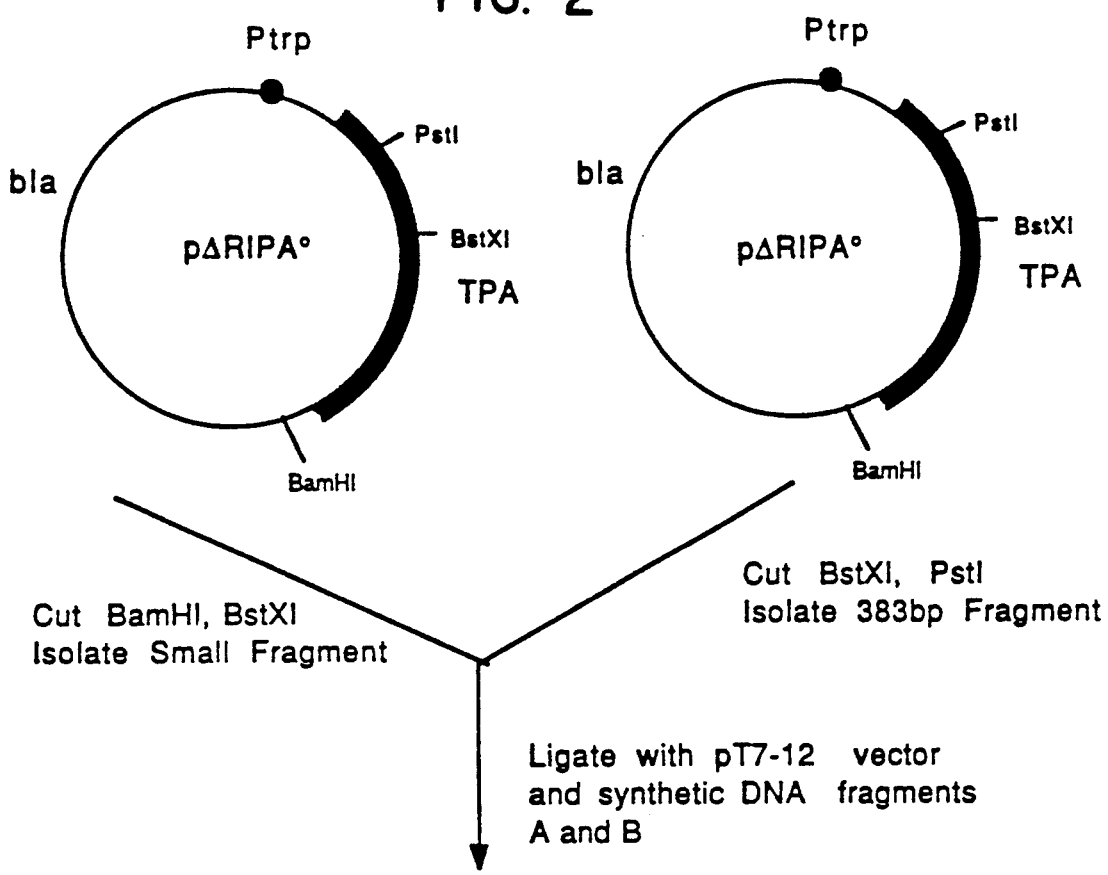
FIG. 2. shows the final steps in the assembly of the pT7-12ST2tPA-1 vector bearing the STII-tPA gene under the transcriptional control of the phi 10 promoter.
Figure 2:
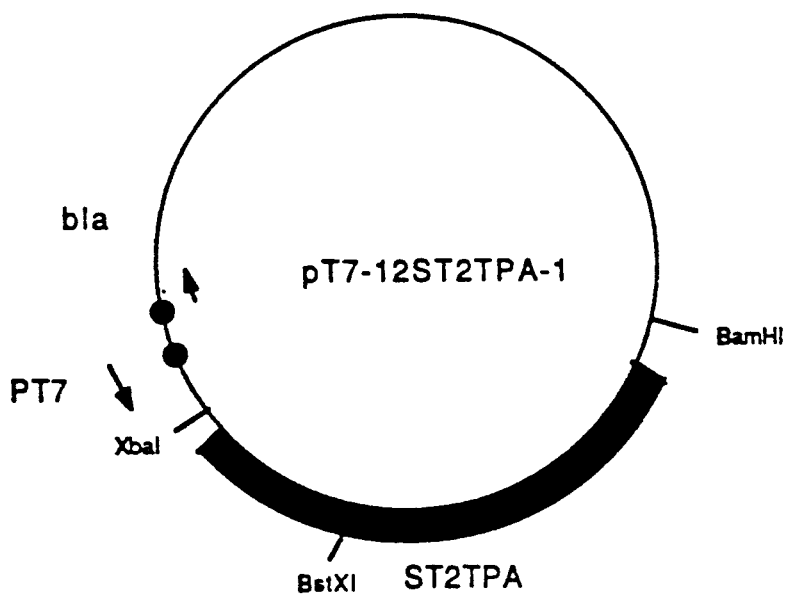

It is conventional to place T7 RNA polymerase under the control of the lac UV5 promoter (Studier et al., supra) or the PL promoter (Tabor et al., supra) in order to provide inducibility for T7 RNA polymerase expression. None of these constructions results in the proper constitutive levels of transcriptional control described herein for pre human t-PA. Another construction (Stahl and Zinn "J. Mol. Biol." 148:481–485 [1981]) has now been found to contain a region located 5' to the RNA polymerase gene that acts as a constitutive promoter.

The plasmid employed by Studier et al. (supra) expressed β-lactamase under the control of the T7 promoter, resulting upon induction of the RNA polymerase in an excessive and toxic accumulation of penicillinase in the host culture. This problem was overcome by excising the relevant T7 promoter and gene from the expression plasmid and reinserting it in the inverted orientation so that transcription from the T7 promoter does not lead to polycistronic transcription of the β-lactamase gene.

Finally, the method of Studier et al. (op cit) introduced the RNA polymerase by phage infection, a devastating event from the perspective of the host cell. Even if the prophage was integrated into the host cell genome, the presence of other lambda promoters leads to unsatisfactory elevated constitutive RNA polymerase expression levels. Accordingly, T7 RNA polymerase was integrated into the recipient host genome under the control of an inducible promoter, in the preferred example the lac operon (lac).

The resulting host-vector system, when cultured under conditions of catabolite repression, provides sufficient suppression of RNA polymerase expression that cotransformants with DNA encoding human t-PA grow normally without plasmid instability or host cell toxicity. The constitutive T7 RNA polymerase activity in the balanced constitutive inducible transcription control system herein is less than that which is produced in the Studier et al. (op cit.) host-vector system, but is inducible to much greater levels than can be obtained using the Tabor et al. T7 system.

The T7 system is of the type referred to herein as a "dedicated RNA polymerase transcriptional control system". In such systems the promoter which controls the transcription of a target gene is not recognized, i.e. transcribed, by endogenous host cell RNA polymerase. Besides the T7 system, phage T3 also uses a dedicated RNA polymerase in its expression of T3 proteins. T3 promoters are commercially available (Stratagene). The T3 polymerase and promoters are employed in the same fashion as described herein for the T7 components, i.e., the T3 polymerase is supplied to the host cell under the control of a balanced constitutive inducible promoter preferably as a single copy chromosomal integrant, while a target gene is placed in a high copy number plasmid under the control of a T3 promoter recognized by the T3 polymerase. Similarly, SP6 polymerase and its promoter (Promega Biotec) are employed in the same fashion as T3 and T7.

Other transcriptional control systems which exhibit the proper balanced constitutive expression levels for stable and effective t-PA synthesis will be within the skill of the ordinary artisan. This invention, insofar as it relates to the expression of t-PA, is not limited to dedicated RNA polymerase transcriptional control systems. Other inducible promoters or promoter systems are suitable provided that the level of constitutive expression is balanced for the host cell and t-PA variant concerned. For example, the λ promoter which requires CII polypeptide (Fein et al. "Gene" 32:141–150 [1984]) is placed under balanced constitutive inducible transcriptional control. A λ promoter which requires CII polypeptide for transcription by endogenous E. coli RNA polymerase is placed in control of the target gene to be expressed. Then, induction of the CII polypeptide will similarly induce transcription from the target gene.

The balanced constitutive transcriptional control system herein is useful in prokaryotic and eukaryotic host cells including bacterial, fungal (including yeast), mammalian or insect cells. Preferably, the system is used with prokaryotes.

Any polypeptide is capable of being expressed under the control of the balanced constitutive transcriptional control system of this invention, "polypeptide" meaning any polyamide including proteins and low molecular weight peptides having greater than one amino acid residue. As noted above, polypeptide which are subject to insolubilization by host cells are candidates for expression and secretion under the control of the improved system of this invention, as are polypeptides which are toxic to the host cell in which they are expressed. Dedicated RNA polymerase transcriptional control systems are especially useful in cases where a balanced control system requires highly nonconstitutive inducible promoter activity.

Typical polypeptides produced using this method include mammalian or bacterial proteins such as enzymes, hormones, and the like, including particularly mammalian enzymes which are normally glycosylated, e.g. human t-PA, growth factors such as TGF-β, hormones such as activin or prorelaxin, bovine rennin, enkephalinase, and the like.

In a preferred embodiment, transcription of preproteins encoding human plasminogen activators is placed under the control of one of the balanced constitutive inducible systems described herein. Plasminogen activators are defined as enzymes which are capable of cleaving plasminogen to produce proteolytically active plasmin. Plasminogen activators include enzymes which bind to fibrin, e.g. tissue plasminogen activator, and those that do not, e.g. urokinase. Also included within the scope of plasminogen activators are engineered amino acid sequence variants not found in nature, e.g., variants in which glycosylation sites are deleted, as well as alleles and animal analogues. The preferred plasminogen activator is full length human t-PA, i.e. t-PA which includes the "finger-domain" occurring at the N-terminus of the enzyme. Single or two-chain forms of t-PA fall within the scope of this invention, as do other amino acid sequence variants. Examples of amino acid sequence variants include des $Arg_{275}$ or other variants as residues 270–279 (EP 199,574).

In the preferred embodiments human t-PA is secreted into bacterial periplasm or culture medium from transformants with DNA encoding the native human pret-PA or a fusion of the E. coli STII signal (EP 177,343) with the mature enzyme. However, selection of other suitable signal sequences would be within the skill of the ordinary artisan; the invention here lies in making it possible to readily determine which signals will be most effective by overcoming the incompatibility of pret-PA with prokaryotic hosts.

The balanced constitutive inducible systems typically are constructed by making and cloning all constructions involving the gene for the heterologous protein in the absence of DNA for the promoter system or a key component thereof, e.g. the T3 or T7 RNA polymerase or CII polypeptide gene, thus enabling one to make the constructions without any danger of selection against the protein, for example upon inadvertent derepression of polymerase or CII polypeptide during cloning. Suitable constructions for the desired heterologous protein then are transfected into the desired host cell bearing DNA for the control system, for example the required polymerase or CII genes (or the polymerase or CII genes are transfected into the host cell bearing the heterologous protein DNA). In the preferred embodiment the gene encoding the heterologous polypeptide is placed under the control of the phi 10 promoter (recognized by the T7 polymerase) or a phage T3 promoter (recognized by the T3 polymerase). The tailored T7 RNA polymerase is present as a host cell integrant in E. coli strain K5772 (deposited in the American Type Culture Collection under accession number 53,635). This strain contains the T7 RNA polymerase gene inserted into the chromosomal lacZ operon which is thus inducible by addition of isopropylthiogalactoside (IPGT) to the media. The constitutive level of expression of T7 RNA polymerase is dependent upon the untranslated domain located 5′ to the polymerase structural gene. The T7 RNA polymerase gene integrated in E. coli K5772 contains the following sequence (the complementary strand is not shown):

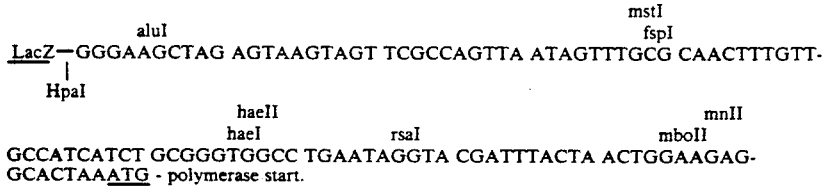

The HpaI site is the first HpaI of the *E. coli* lacZ.

The balanced constitutive inducible promoter system developed for the secretion of human t-PA from prokaryotes required the introduction of modifications into conventional T7 RNA polymerase vectors, more specifically into the promoter controlling transcription of the T7 RNA polymerase. The lac UV5 promoter of Studier et al. (supra) modified $P_L$ promoter could not be sufficiently induced because of the insertion of a terminator, and the Stahl et al. (supra) vector contained an excessively active promoter function of unclear origin located 5' to the T7 RNA polymerase. These inadequacies were overcome by placing the T7 RNA polymerase gene under the control of the wild type lacZ promoter and culturing transformants in the presence of glucose. This wild type lac promoter is constitutively transcribed under catabolite repression at a level which is about 10% of the lac UV5 promoter. The wild type lac promoter is induced about 10 times by catabolite depletion (glucose depletion), and is induced further by adding IPTG to the culture. Without glucose, transcription is excessive, i.e. the lac operon is not sufficiently repressed and t-PA is not secreted. The regulated constitutive level of pret-PA expression achieved with this system has permitted the large scale culture of stable transformants which then can be induced with ITPG or other suitable agent. As a further improvement, lacI$^q$ host cells are chosen. These cells overproduce the lac repressor, thus further ensuring that the constitutive expression of pret-PA is sufficiently low to be compatible with the host cell.

The level of constitutive expression from the STII-t-PA preprotein using the lacZ promoted T7 RNA polymerase system described herein was found to be compatible with *E. coli* K5772 cells. However, it will be appreciated that the optimal expression level of this preprotein, as tolerated by this host, will be determined by the ordinary artisan by appropriate manipulation of preprotein transcription levels. Other host cells and constructions encoding other proteins or preproteins will require balancing the constitutive expression with plasmid stability and host cell toxicity. This is most conveniently accomplished by simply measuring the constitutive mature protein secretion or protein synthesis levels over about from 10 to 50 generations of the transformant. If these constitutive levels are not stable, then the transcription rate of the DNA encoding the preprotein or protein is reduced by further repressing the transcriptional system or by replacing the transcriptional control system entirely with another having an appropriate rate of transcription. On the other hand, if the transformants are stable then the system is modified in the direction of increased constitutive transcription until instability for the selected host-vector system is reached.

The balanced constitutive inducible promoter system is induced at any appropriate point in the host culture cycle, preferably later in the cycle such as the stationary phase or late log phase when cell density is reaching maximum levels. Induction should be rapid rather than progressively phased.

The process of this invention now has facilitated the secretion of full length, mature human t-PA in soluble form which is fully biologically active, i.e. which in the presence of fibrin and plasminogen exhibits proteolytic activity increases of about 10 to 30 times and which is capable of binding to lysine Sepharose. The human t-PA of this invention is unglycosylated yet is soluble and exhibits high specific activity. In addition, in the preferred embodiment it contains the finger region located between residues 1 and 44, and ordinarily the novel t-PA of this invention contains the complete amino acid sequence variants, especially substitutional variants, also are included within the scope of t-PA as produced by the method herein.

The t-PA is secreted into prokaryotic host periplasm at levels of specific activity exceeding about 2 S-2251 units at $A_{405}$/min/$\mu$g of t-PA protein as determined by enzyme linked immunoabsorbent assay (ELISA). Specific activity typically ranges about from 2 to 10 S-2251 units. This degree of specific activity is comparable to that of recombinant t-PA secreted from mammalian cell culture and far exceeds the activity of non-secreted met-PA obtained from the cytoplasm of prokaryotic transformants. It was surprising and unexpected that unglycosylated human t-PA would be soluble in aqueous media (10 mM Tris pH 8 and 0.5 m arginine) at concentrations exceeding 50 $\mu$g/ml and yet retain the salient enzymological functions of the glycosylated form of the molecule.

The secreted t-PA herein is recovered from the periplasmic space by conventional methods, e.g. isotonic or cold shock. Measures desirably are taken during recovery of the t-PA in order to protect it from hydrolysis by endogenous host proteases, e.g. by flooding the recovery solutions with an innocuous substrate peptide to swamp out adventitious proteolytic enzymes and by conducting the recovery as rapidly as possible to avoid exposing the t-PA to cytoplasmic proteases. Alternatively, host cells are selected for an absence of interfering proteases.

In order to simplify the Examples certain frequently occurring methods will be referenced by shorthand phrases.

"Plasmids" are designed by a low case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designated the particular enzyme. In general, about 1 μg of plasmid or DNA fragment is used with about 2 units of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of the marker DNA fragments of known molecular weight removal of the gel section containing the desired fragment, and separation of the gel from DN. This procedure is known generally. For example, see R. Lawn et al., 1981, "Nucleic Acids Res." 9:6103–6114, and D. Goeddel et al., 1980, "Nucleic Acids Res." 8:4057.

"Transformation" or "transfection" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., 1970, "J. Mol. Biol." 53:154.

"Ligation" refers to the process of forming phosphodiester bonds between two double stranded nucleic acid fragments (T. Maniatis et Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

All literature citations herein are expressly incorporated by reference.

EXAMPLE

Construction of pT7-12

Plasmid pT7-2 was obtained from United States Biochemical Corporation. The plasmid DNA was cleaved with PvuI and religated. The DNA was used to transform competent bacteria and clones screened for inversion of the PvuI fragment. One such inverted clone was called pT7-12. The purpose of this construction was to prevent high-level expression of the beta-lactamase gene, which otherwise would be transcribed under the control of the phi 10 promoter.

Construction of pT7-12ST2HGH

Plasmid pT7-12 was digested with HinCII and BamHI and the large vector fragment isolated. Plasmid ptrpST2HGH (EP 177,343) was digested with HpaI and BamHI and the small hGH coding fragment isolated. The two fragments were ligated to produce pT7-12ST2HGH.

Construction of PT7-12ST2t-PA

Plasmid pT7-12ST2HGH was digested with XbaI and BamHI and the large vector fragment isolated. Plasmid pΔRIPA° (EP 93,619, containing the *E. coli* trp promoter/operator and the human t-PA gene) was digested with BstXI and BamHI and the small fragment (the t-PA gene) isolated. The same plasmid was also cleaved with BstXI and PstI and the 383bp fragment isolated. These three fragments were ligated with two double-stranded synthetic DNA fragments A (the N-terminus of the STII signal) and B (encoding the C-terminus of the STII signal fused to the N-terminal seryl residue of t-PA) to yield pT7ST2t-PA-1.

```
XbaI                                                                                          MluI
CTAGAATTATGAAAAAGAATATCGCATTTCTTCTTGCATCGATGTTCGTTTTTTCTATTGCTACAAA
    TTAATACTTTTTCTTATAGCGTAAAGAAGAACGTAGCTACAAGCAAAAAAGATAACGATGTTTGCGCp
    MetLysLysAsnIleAlaPheLeuLeuAlaSerMetPheValPheSerIleAlaThrAsn
```

Fragment A

```
    MluI                              PstI
pCGCGTATGCATCTTACCAAGTGATCTGCA
    ATACGTAGAATGGTTCACTAG
    AlaTyrAlaSerTyrGlnValIleCys
```

Fragment B

Introduction of pT-12ST2t-PA into an Expression Host

K5772 bacteria were made competent and transformed with pT7-12ST2t-PA-1 by selecting for resistance to ampicillin. The transformed bacteria were maintained on media containing glucose to lower expression by catabolite repression of the lac operon, which controls the level of T7 RNA polymerase.

Expression and Secretion of ST2t-PA in *E. coli*

K5772 containing pT7-12ST2t-PA-1 (K5776) was grown at 37° C. to saturation in 1 liter of M9-glucose -casamino acid media with ampicillin, the cell pellet collected by centrifugation and stored at −20° C. The presence of glucose ensures catabolite repression of the lac promoter controlling T7 RNA polymerase transcription. Appreciable levels of ST2t-PA were produced even under conditions of constitutive repression by glucose; addition of IPTG to the culture resulted in the expression of greater quantities of t-PA as adjudged by gel electrophoresis of cell extracts.

Extraction of t-PA from the Periplasm

The cell pellet was thawed and resuspended in an aqueous solution containing 0.1M Tris-HCl pH8, 0.05M EDTA, and 0.5M sucrose at a cell density of 250 OD units/ml at 0° C. The cells were stirred for 10 min. The cells were centrifuged and the supernatant discarded. The pellet was resuspended in 10 mM Tris-HCl pH8 at 250 OD units/ml. Once the pellet was resuspended, solid arginine-HCl was added to produce a concentration of 0.5M (105 g/l). The suspension was stirred for 2 hr. at 0° C. after which the cells were removed by successive centrifugation at 12,000×g for 20 min.

Purification of the Periplasmic Extract

An antibody-sepharose column of rabbit polyclonal anti-CHO-tPA antibody was equilibrated with 0.1M HEPES pH7.5, 0.5M Arginine. The $E.$ $coli$ periplasmic extract, in the same buffer, was loaded on the column. The column was washed with 50 mM Tris pH7.5, 1M NaCl until no further protein (as detected by an in-line absorbance monitor) was in the wash. The t-PA then was eluted with 0.1M Acetic acid, 0.15M NaCl pH3, the peak collected and the t-PA solution titrated to pH 7 with 2N KOH.

Assays for t-PA

(a) Specific Activity and Fibrin Stimulation

The purified extract was assayed for specific activity by S-2251 with fibrinogen to determine activated plasmin activity and by ELISA for t-PA protein to determine the amount of t-PA responsible for the activity. Assays without fibrinogen were used to determine fibrin stimulation. The reaction mixture contained 30 μl of a plasminogen solution (2.1 mg/ml) with or without fibrinogen (20 μl of a 20 mg/ml solution) in a final total volume of 150 μl of 0.05M Tris-HCl, pH 7.4, 0.12M sodium chloride, and 0.01% Tween 80. A total of 10 μl of the sample to be tested was added, containing 2-5 ng of enzyme for reactions with fibrinogen and between 0.05 and 2 μg for reactions without fibrinogen. The reaction was allowed to proceed for 10 min at 37° C. The reaction mixture was diluted with 0.35 ml of 0.86 mM H-D-valyl-L-leucyl-L-lysine-p-nitroanilide (S-2251) dissolved in 36 mM Tris, 0.086M NaCl, and 0.007% Tween 80. Plasmin cleavage of the S-2251 was allowed to proceed for 5 min, and the reaction was terminated by the addition of 25 μl of glacial acetic acid. The extent of plasmin formation was determined by the absorbance of the sample at 405 nm. A "unit" of S-2251 is defined as 1 $A_{405}$/min/μg t-PA protein.

The ELISA for t-PA was conducted as follows:

The wells of plastic microtiter plates were coated with goat anti-CHO-tPA polyclonal antibody by adding 100 microliters of antibody in coating buffer (0.05M sodium carbonate pH9.6) to each well and incubating at 4° C. for 12 hrs. "CHO-tPA" is essentially homogeneous human t-PA secreted by and recovered from the culture media of recombinant Chinese Hamster Ovary cells transformed with the gene for human t-PA. The wells were washed three times with 200 μl wash buffer (0.01M sodium phosphate pH 7.4(PBS), 0.05% Polysorbate 80), 200 μl of assay diluent are added to each well and incubated for one hr. at room temperature with agitation. The assay diluent was PBS, 0.5% Bovine Serum Albumin, 0.01% Polysorbate 80, 0.01% Thimersol. The wells were washed again with wash buffer. CHO-tPA standards, untransformed $E.$ $coli$ periplasmic extract and samples of periplasmic t-PA extracts were added in 100 μl of assay diluent to the wells and incubated at room temperature with agitation for 2 hr, after which the wells were washed with wash buffer. 100 μl of goat polyclonal anti-tPA-HRP conjugate in assay diluent were added to each well and incubated at room temperature for 1 hr with agitation, followed by another wash. 100 μl of HRP substrate was added to each well and incubated for 20 min in the dark at room temperature. HRP substrate is 0.04% o-phenylene-diamine, 0.1M Citric Acid, 0.2M sodium phosphate pH 5, 0.12% Hydrogen Peroxide. 100 μl of 4.5N sulfuric acid was added to each well and the adsorbances were read at 492 nm. The sample values are compared with the standard curve.

The secreted $E.$ $coli$ t-PA appears to increase in titer in this assay as the dilution is increased. This is attributed to the presence of water soluble multimers of the t-PA at high concentration which are detected by the ELISA assay as monomers. Therefore, the samples must be diluted until the point is reached where no further increase in titer is seen with increasing dilution or this must be extrapolated from available date. The t-PA concentration determined in this manner is used in the specific activity determination.

A μg of t-PA protein is defined as the amount of t-PA giving the same $A_{492}$ as the 1 μg standard.

The purified extract was found to contain 3.9 S-2251 $A_{405}$ units/min./μg of t-PA protein. The yield of t-PA was 1 mg/l.

(b) Lysine Binding

A column of lysine-sepharose was equilibrated with 50 mM sodium phosphate buffer pH 7.5. The purified extract was dialyzed into 25 mM Tris pH8/0.5M NaCl and loaded on the column. The column then was washed with 40Mm Tris pH8/0.5M NaCl and bound protein eluted with 50 mM sodium phosphate buffer pH7.5/0.2M arginine. Column fractions were assayed for t-PA activity by fibrin plate assay. The results of this study demonstrated that >90% of the total loaded t-PA activity bound to the lysine column.

I claim:

1. A method for the secretion of biologically active human t-PA from $E.$ $coli$ host cell transformants in commercially significant quantities comprising:
    a) transforming lacI$^q$ $E.$ $coli$ host cells containing nucleic acid encoding T7 RNA polymerase unaccompanied by 5' untranslated region conferring low level constitutive transcriptional activity on said nucleic acid, under the transcriptional control of the wild-type lacZ promoter, with an expression vector containing nucleic acid encoding a human t-PA preceded by the $E.$ $coil$ STII signal sequence under the transcriptional control of the phi 10 promoter,
    b) culturing the transformants in the presence of glucose until a desired cell density is reached, and
    c) inducing said inducible wild-type lacZ promoter thereby initiating transcription from said DNA encoding human t-PA preceded by the $E.$ $coli$ STII signal sequence, and
    d) recovering mature human t-PA from the cell periplasm, or cell culture medium.

2. The method of claim 1 wherein the host cell is $E.$ $coli$ strain K5772.

* * * * *